US011167009B2

(12) United States Patent
Castellano et al.

(10) Patent No.: US 11,167,009 B2
(45) Date of Patent: Nov. 9, 2021

(54) THERAPEUTIC METHOD OF TREATMENT FOR INHIBITING TUMOR DEVELOPMENT USING TAMM-HORSFALL GLYCOPROTEIN (THP) AS IMMUNOSTIMULATING DRUG AND COMPOSITIONS

(71) Applicants: INSTITUTO MASSONE S.A., Buenos Aires (AR); Raúl Enrique Massone, Buenos Aires (AR)

(72) Inventors: Miguel Angel Castellano, Montevideo (UY); José F. Groisman, Buenos Aires (AR); Liliana Ester Balanian, Buenos Aires (AR); Felipe Inserra, Buenos Aires (AR); Emilio Sojo, Prov. de Buenos Aires (AR); Claudio Fernando Wolfenson Band, Buenos Aires (AR); Elena M. V. de Cavanagh, Martínez (AR)

(73) Assignees: INSTITUTO MASSONE S.A., Buenos Aires (AR); Raúl Enrique Massone, Buenos Aires (AR)

( * ) Notice: Subject to any disclaimer, the term of this patent is extended or adjusted under 35 U.S.C. 154(b) by 0 days.

(21) Appl. No.: 15/204,033

(22) Filed: Jul. 7, 2016

(65) Prior Publication Data
US 2016/0310568 A1 Oct. 27, 2016

Related U.S. Application Data

(62) Division of application No. 14/377,575, filed as application No. PCT/IB2013/051053 on Feb. 8, 2013, now abandoned.

(60) Provisional application No. 61/596,863, filed on Feb. 9, 2012.

(51) Int. Cl.
A61K 38/17 (2006.01)
A61K 38/16 (2006.01)
A61P 35/00 (2006.01)

(52) U.S. Cl.
CPC .......... *A61K 38/1709* (2013.01); *A61K 38/16* (2013.01); *A61P 35/00* (2018.01); *Y02A 50/30* (2018.01)

(58) Field of Classification Search
CPC ..... A61K 38/1709; A61K 38/16; A61P 35/00; Y02A 50/30
See application file for complete search history.

(56) References Cited

U.S. PATENT DOCUMENTS 5,595,756 A * 1/1997 Bally .................. A61K 9/1272
264/4.1
2009/0023637 A1 1/2009 Parsons
2009/0275521 A1* 11/2009 Meyer-Siegler ... A61K 38/1709
514/1.1
2009/0280111 A1 11/2009 Zheng et al.

OTHER PUBLICATIONS

Cellular and Molecular Basis of Cancer, from http://www.merckmanuals.com/professional/print/hematology_and_oncology/overview_of . . . , pp. 1-5, accessed Nov. 7, 2012.*
Sporn, B and Suh, N, Chemoprevention of cancer, Carcinogenesis, 2000, 21, pp. 525-530.*
Auerbach. R. et al, Angiogenesis assays: Problems and pitfalls, Cancer and Metastasis Reviews, 2000, 19, pp. 167-172.*
Gura, T. Systems for Identifying New Drugs Are Often Faulty, Science, 1997, 278, pp. 1041-1042.*
Jain R. K., Barriers to Drug Delivery in Solid Tumors, Scientific American, 1994, pp. 58-65.*
Cancer Drug Design and Discovery. Neidle, Stephen, ed., Elsevier/ACademic Press, 2008, p. 427-431.*
Halt, Anticancer drug development: the grand challenges, Nature Reviews/Drug Discovery, 2010, 9, pp. 253-254.*
Gravanis et al, The changing world of cancer drug development: the regulatory bodies' perspective, Chin Clin Oncol, 2014, 3, pp. 1-5.*
So et al, The application of Toll like receptors for cancer therapy, Int. J. Biol. Sci., 2010, 6, pp. 675-681.*
Andreani et al, Activation of Toll-like Receptor 4 on Tumor Cells In vitro Inhibits Subsequent Tumor Growth In vivo, Cancer Res, 2007, 67, p. 10519-10527.*
Hironaka et al, Essential Requirement of Toll-like Receptor 4 Expression on CD11c+ Cells for Locoregional Immunotherapy of Malignant Ascites Using a Streptococcal Preparation OK-432, Anticancer Research, 2006, 26, pp. 3701-3708.*
Kelly et al, TLR-4 Signaling Promotes Tumor Growth and Paclitaxel Chemoresistance in Ovarian Cancer, Cancer Res, 2006, 66, pp. 3859-3868.*
Subik et al, The Expression Patterns of ER, PR, HER2, CK5/6, EGFR, Ki-67 and AR by Immunohistochemical Analysis in Breast Cancer Cell Lines, Breast Cancer: Basic and Clinical Research, 2010, 4, pp. 35-41.*
Yang et al, Estradiol increases ER-negative breast cancer metastasis in an experimental model, Clin Exp Metastasis, 2013, 30, pp. 711-721.*
Chavez et al, Triple negative breast cancer cell lines: One tool in the search for better treatment of triple negative breast cancer, Breast Disease, 2010, 32, pp. 35-48.*

(Continued)

*Primary Examiner* — Li N Komatsu
(74) *Attorney, Agent, or Firm* — Nixon & Vanderhye

(57) ABSTRACT

The present invention relates to a pharmaceutical composition for inhibiting tumor development, which comprises Tamm-Horsfall glycoprotein, native or pegylated and a pharmacologically acceptable excipient, therapeutic methods and uses.

3 Claims, 13 Drawing Sheets

(56) References Cited

OTHER PUBLICATIONS

Adenocarcinoma, from https://www.cancercenter.com/terms/adenocarcinoma, pp. 1-3, accessed Feb. 12, 2018.*
Adenocarcinoma: Types, diagnosis, and treatment, from https://www.medicalnewstoday.com/articles/318734.php, pp. 1-12, accessed Feb. 12, 2018.*
Kiesler, Why a New Immunotherapy for Lung Cancer Works for Only Some People, from https://www.mskcc.org/blog/why-new-immunotherapy-lung-works-only-some-people, Apr. 16, 2015, pp. 1-4.*
Sahin et al, Immunotherapy in pancreatic ductal adenocarcinoma: an emerging entity?, Annals of Oncology, 2017, 28, pp. 2950-2961.*
Xu et al, Overexpression of macrophage migration inhibitory factor induces angiogenesis in human breast cancer, Cancer Letters, 2008, 261, pp. 147-157.*
MDA-MB-231, from https://www.atcc.org/Products/All/HTB-26.aspx?&p=1&rel=generalinformation, p. 1, accessed Feb. 12, 2018.*
Lewis et al, Macrophage Responses to Hypoxia-Implications for Tumor Progression and Anti-Cancer Therapies, American Journal of Pathology, 2005, 167, pp. 627-635.*
4T1, from https://www.atcc.org/en/Products/All/CRL-2539.aspx?&p=1&rel=generalinformation, p. 1, accessed Jan. 31, 2019.*
Tao et al, Imagable 4T1 model for the study of late stage breast cancer, BMC Cancer, 2008, 8, pp. 1-20.*
Gatti et al, Expression of Toll-Like Receptor 4 in the Prostate Gland and Its Association With the Severity of Prostate Cancer, The Prostate, 2009, 69, pp. 1387-1397.*
Meyer-Siegler et al, Inhibition of macrophage migration inhibitory factor decreases proliferation and cytokine expression in bladder cancer cells, BMC Cancer, 2004, 4, pp. 1-12.*
Verjans et al, Dual role of macrophage migration inhibitory factor (MIF) in human breast cancer, BMC Cancer, 2009, 9, pp. 1-18.*
Cho et al., "Optimized Clinical Performance of Growth Hormone With an Expanded Genetic Code", Proceedings of the National Academy of Sciences USA, vol. 108, No. 22, pp. 9060-9065, 2011.
Bailon et al., "Rational Design of a Potent, Long-Lasting Form of Interferon: A 40 kDa Branched Polyethylene Glycol-Conjugated Interferon a-2a for the Treatment of Hepatitis C" Bioconjugate Chem. 2001, 12, pp. 195-202.
Fishburn, "The Pharmacology of PEGylation: Balancing PD With PK to Generate Novel Therapeutics", Journal of Pharmaceutical Sciences, 97 (10), 4167, 2008.
Schmidt et al., "PEGylated Bioactive Molecules in Biodegradable Polymer Microparticles", Expert Opinion on Biological Therapy, 7, 2007, pp. 1427-1436.
Chen et al., "Modulating Antibody Pharmacokinetics Using Hydrophilic Polymers", Expert Opinion on Drug Delivery, 8, 1221, 8, pp. 1221-1236, 2011.
Hu et al., "PEGylation of VAL-1(a) Destabilizes the Tetrameric Structure of Hemoglobin", Biochemistry 2009, 48, pp. 608-616.
Wang et al., "Immunogenicity of Protein Aggregates—Concerns and Realities", International Journal of Pharmaceutics, 431 (2012) pp. 1-11.
Pasut et al., "PEGylation for Improving the Effectiveness of Therapeutic Biomolecules" Drugs of Today 2009, 45(9) pp. 687-695.
Matthews, "Investigation Into the Effects of PEGylation on the Thermodynamic Stability of the WW Domain", Brigham Young University Scholars Archive, Dec. 1, 2013, Paper 4280.
International Search Report dated May 2, 2013 in International Application No. PCT/IB2013/051053.

Saemann et al, Tamm-Horsfall glycoprotein links innate immune cell activation with adaptive immunity via a Toll-like receptor-4-dependent mechanism, J Clin Invest, 2005, 115, pp. 468-475.
Water, from http://www.biology-online.org/dictionary/Water, pp. 1-3, accessed Apr. 24, 2014.
Veronese et al, PEGylation, successful approach to drug delivery, DDT, 2005, 10, pp. 1451-1458.
Ahmed et al., "Silencing of TLR4 Increases Tumor Progression and Lung Metastasis in a Murine Model of Breast Cancer," Annals of Surgical Oncology, 20(3), Aug. 2012.
Ahmed et al., "Links between Toll-like receptor 4 and breast cancer," OncoImmunology 2:2, e22945; Feb. 2013.
Ellis et al., "Role of Angiogenesis Inhibitors in Cancer Treatment," Oncology 15, Issue 7(Suppl 8):39-46, 2001.
Giantonio et al., "Bevacizumab in Combination With Oxaliplatin, Fluorouracil, and Leucovorin (FOLFOX4) for Previously Treated Metastatic Colorectal Cancer: Results From the Eastern Cooperative Oncology Group Study E3200," Journal of Clinical Oncology, vol. 25, No. 12, Apr. 20, 2007, pp. 1539-1544.
Harmey et al., "Lipopolysaccharide-Induced Metastatic Growth is Associated with Increased Angiogenesis, Vascular Permeability and Tumor Cell Invasion," International Journal of Cancer 101, 415-422 (2002).
Hurwitz et al., "Bevacizumab plus Irinotecan, Fluorouracil, and Leucovorin for Metastatic Colorectal Cancer," vol. 350, No. 23, Jun. 3, 2004, pp. 2335-2342.
Liao et al., "Triggering of Toll-like receptor 4 on metastatic breast cancer cells promotes αvβ3-mediated adhesion and invasive migration," Breast Cancer Research and Treatment (2012) 133:853-863.
Ma et al., "Dominant Effect of Anti-angiogenesis in Combination Therapy Involving Cyclophosphamide and the VEGF Receptor Tyrosine Kinase Inhibitor Axitinib," Clinical Cancer Research, Jan. 15, 2009; 15(2): 578-588.
Papageorgiou et al., "Combination therapy with IFN-α plus bortezomib induces apoptosis and inhibits angiogenesis in human bladder cancer cells," Molecular Cancer Therapeutics, Dec. 2006;5(12), pp. 3032-3041.
Qian et al., "The Histone Deacetylase Inhibitor NVP-LAQ824 Inhibits Angiogenesis and Has a Greater Antitumor Effect in Combination with the Vascular Endothelial Growth Factor Receptor Tyrosine Kinase Inhibitor PTK787/ZK222584," Cancer Research 64, 6626-6634, Sep. 15, 2004.
Rajabi et al., "The Role of Angiogenesis in Cancer Treatment," Biomedicines 2017, 5, 34.
Saemann et al., "Tamm-Horsfall glycoprotein links innate immune cell activation with adaptive immunity via a Toll-like receptor-4-dependent mechanism," The Journal of Clinical Investigation, vol. 115, No. 2, Feb. 2005, pp. 468-475.
Verheul et al., "Possible molecular mechanisms involved in the toxicity of angiogenesis inhibition," Nature Reviews Cancer, vol. 7, Jun. 2007, pp. 475-485.
Wu et al., "Intact protein core structure is essential for protein-binding, mononuclear cell proliferating, and neuteophil phagocytosis-enhancing activities of normal human urinary Tamm-Horsfall glycoprotein," International Immunopharmacology (2008) 8, 90-99.
Yang et al., "Reduced expression of Toll-like receptor 4 inhibits human breast cancer cells proliferation and inflammatory cytokines secretion," Journal of Experimental & Clinical Cancer Research 2010, 29:92.
Zhao et al., "Metadherin Mediates Lipopolysaccharide-Induced Migration and Invasion of Breast Cancer Cells," PLoS ONE, Dec. 2011, vol. 6, issue 12, e29363.

* cited by examiner

* Ulcerated tumor

Fig 8
A
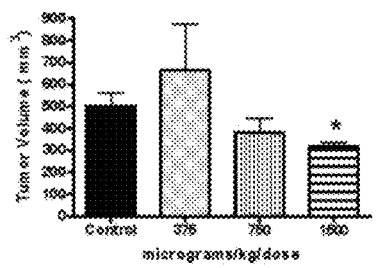
B
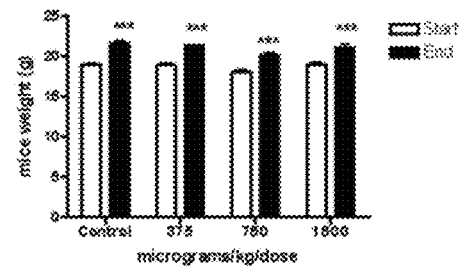
C
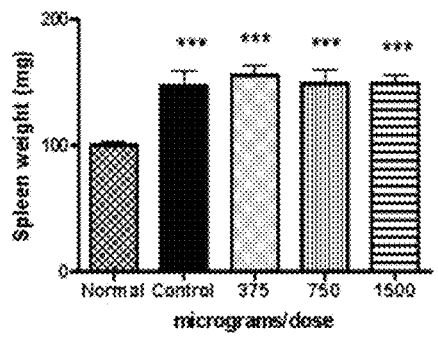

THERAPEUTIC METHOD OF TREATMENT FOR INHIBITING TUMOR DEVELOPMENT USING TAMM-HORSFALL GLYCOPROTEIN (THP) AS IMMUNOSTIMULATING DRUG AND COMPOSITIONS

The instant application is a divisional application of U.S. application Ser. No. 14/377575, filed on Aug. 8, 2014, currently abandoned, which is a 371 of PCT/IB2013/051053 filed on Feb. 8, 2013, and claims benefit of US provisional application No. 61/596863 filed on Feb. 9, 2012.

The present invention relates to use of THP (human urinary Tamm-Horsfall glycoprotein) (UniProtKB/Swiuss-Prot P07911) (THP) and a method of treatment for inhibiting tumor development using Tamm-Horsfall glycoprotein.

The ability to improve the resistance to tumors and infections is reported in this application.

Highly purified human urinary protein, homogeneous in polyacrilamide gel electrophoresis is used. Identification of the protein is performed by molecular weight determination, amino acid sequencing in the protein fraction, and enzyme linked immuno-assay.

THP was obtained as a by-product of hCG or hMG production (THP-hCG, THP-hMG).

Vials used contain 4.8 mg of freeze-dried protein and 200 mg lactose, and Tris base 50 mg.

Product is a white powder, free of pyrogens. Molecular weight of the protein is about 90 kDa. A pegylated form of the protein also was tested.

The resulting pharmaceutical composition (vials) is administrated parenterally.

Previous therapeutic uses of THP are not known.

BACKGROUND OF THE INVENTION

The Tamm-Horsfall glycoprotein (THP) also known as THP is a glycoprotein that in humans is encoded by the UMOD gene. Up to 150 mg/day of THP may be excreted in the urine, making it the most abundant protein in normal urine.

THP is a GPI-anchored glycoprotein. It is not derived from blood plasma but is produced by the thick ascending limb of the loop of Henle of the mammalian kidney. While the monomeric molecule has a MW of approximately 90 kDa, it is physiologically present in urine in large aggregates of up to several million Da. When this protein is concentrated at low pH, it forms a gel. Tamm-Horsfall protein is a high abundant protein in mammalian urine. It is the matrix of urinary casts derived from the secretion of renal tubular cells.

Publications of Weichhart, T., Zlabinger, G J, and Säemann, M D., (The multiple functions of Tamm-Horsfall protein in human health and disease: A Mistery Clears Up, Wien Klin Wochenschr, 117, 316-322, 2005) and Tsai-Hung, W, Song-Chou, H, Chih-Yao, Y, Yi-Fang, L, Chang-Youh, T, Chia-Li, Y (Intact protein core structure is essential for protein binding, mononuclear cell proliferating, and neutrophil phagocytosis-enhancing activities of normal human Urinary Tamm-Horsfall glycoprotein, Intern. Immunopharmacology, 8, 90-99, 2008) showed the immunostimulating effect of Tamm-Horsfall protein.

U.S. Pat. No. 4,977,244 relates to processes for producing THP, a glycoprotein having a molecular weight of 85 kilo daltons. This glycoprotein, which is isolated from crude urine, as well as its carbohydrate derivatives are useful as immunosuppressive agents or anti-inflammatory agents. U.S. Pat. No. 6,110,688 refers to a process for purifying Tamm-Horsfall glycoprotein or THP, their purified products and method for making the discrimination between both of them.

SUMMARY OF THE INVENTION

One object of the present invention is to provide a pharmaceutical composition for inhibiting tumor development, which comprises Tamm-Horsfall glycoprotein, native or pegylated and a pharmacologically acceptable excipient.

Another object of present invention is to provide a therapeutic method of treatment for inhibiting tumor development in mammal, which comprises parenterally administering to a mammal a composition comprising an effective amount of Human Tamm-Horsfall protein, native or pegylated, and a pharmacologically acceptable excipient.

Another object of present invention is to provide a therapeutic method of treatment for increasing the immune innate response in mammals, which comprises parenterally administering to a mammal a composition comprising an effective amount of Human Tamm-Horsfall protein, native or pegylated, and a pharmacologically acceptable excipient.

Another object of the present invention is to provide the use of Tamm-Horsfall glycoprotein, native or pegylated, for preparing a composition for inhibiting tumor development in mammals.

Another object of the present invention is to provide an use of Tamm-Horsfall glycoprotein, native or pegylated, for preparing of a composition for increasing the immune innate response in mammals.

BRIEF DESCRIPTION OF THE DRAWINGS

FIG. 8 corresponds to graphs showing the effect of THP administration on mice bearing CT26 colon cancer of the Report of antitumor effect of THP. When tumors reached $88.6 \pm 12.0$ mm$^3$ (day 1) THP was administrated s.c. at 375, 750 and 1500 mg/kg/day three times every other day, and on day 7 animals were sacrificed. (A) Tumor volume at day 7. *P<0.05. (B) Animal weight at the start (day 1) and at the end (day 7) of the experiment. *P<0.001. (C) Spleen weight *P<0.001. Data are shown as mean±SEM (n=5).

DETAILED DESCRIPTION OF THE INVENTION

Figure 1:
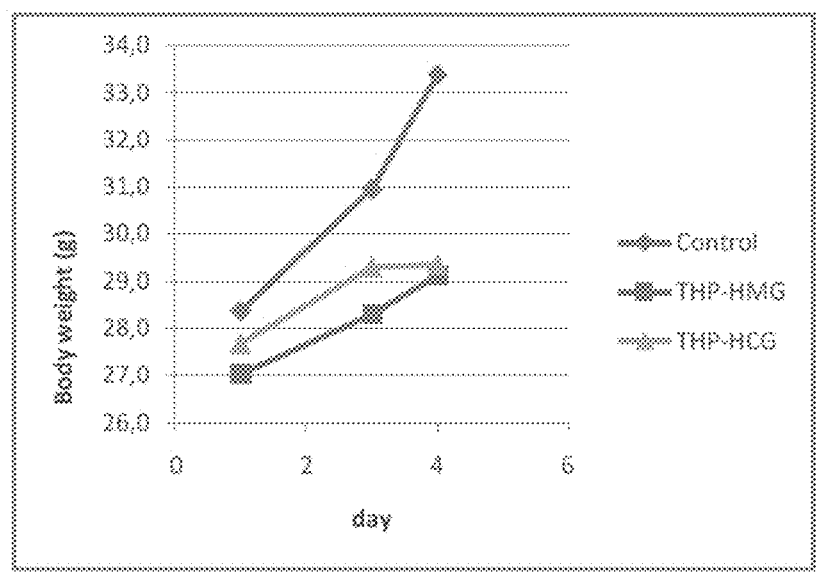
FIG. 1 is a graph depicting Body weight vs. day for Control, THP-HMG and THP-HCG of ASSAY 1.

Immunodeficiency (or immune deficiency) is a state in which the immune system's ability to fight infectious disease is compromised or entirely absent. Immunodeficiency may also decrease cancer immunesurveillance. Most cases of immunodeficiency are acquired ("secondary") but some people are born with defects in their immune system, or primary immunodeficiency. Transplant patients take medications to suppress their immune system as an anti-rejection measure, as do some patients suffering from an over-active immune system. A person who has an immunodeficiency of any kind is said to be immunocompromised. An immunocompromised person may be particularly vulnerable to opportunistic infections, in addition to normal infections that could affect everyone.

Studies performed in the present application demonstrate that the treatment with native or pegylated THP increases the immune innate response in mammals and moreover inhibits tumor development in mammals.

THP was prepared according to the following method:

Method Disclosed by the Paper "Rapid Isolation of Tamm-Horsfall Glycoprotein (Uromodulin) from Human Urine":

Franca Serafini-Cessi, Guivanni Bellabarba, Nadia Malagolini and Fabio Dall'Olio, Journal of Immonological methods, 120 (1989) page 185-189.

THP was isolated from human urine (human pregnancy urine or human post-menopausal urine) according to the procedure detailed by the authors of the above mentioned paper.

The method is based on THP tendency to form a gel in the presence of mono and divalent ions and the ability of diatomaceous earth filter to retain selectively most of the (T-H) glycoprotein present in normal human urine and then its desorption from the filter by deionized water.

Endotoxins were removed from (T-H) glycoprotein by Anion Exchange Chromatography using DEAE-Sepharose as a gel, and buffer 40 mM Tris/ClH pH 8.5 as a mobile phase.

The protein was eluted from the column with 2 bed volumes of 40 mM Tris/ClH pH 8.5 and finally the eluted (T-H) glycoprotein was filtered by 0.22 Millipore filter to obtain a sterile solution.

The solution was aliquoted in falcon tubes×10 ml and was lyophilized.

Physico-Chemical Characterization of Lyophilized Solution:

Each lyophilized vial was resuspended in an appropriate volume of water to obtain a solution 1 mg/ml.

Protein content was done by two methods: Lowry and Size exclusion chromatography by HPLC using a TSK-30 column and 50 mM Tris pH 7.5+10 mM EDTA +0.025% polyoxyethylene (20) sorbitan monolaurate (TWEEN® 20).

Molecular weight and purity of isolated glycoprotein was determined by SDS-PAGE, Coomassie and Silver staining.

Briefly for electrophoretic separation the following equipment and chemicals were used:

LMW calibration mixture from Pharmacia Code N$^a$ 17-0446-01

Phastgel gradient 8-25% SDS Code N° 17-0542-01

Phastgel SDS Buffer strips Code N° 17-0516-01

Sample buffer for SDS-page (10 mM tris/HCl, 1 mM EDTA, pH 8.0+2.5% SDS+5% Mercaptoethanol+0.01% Bromphenolblue)

Equipment

Electrophoresis: Phast System, Pharmacia

Scanner with Software: ImageMaster 1 D, Version 1.10, Sharp JX 325

Under reducing conditions with dithiothreitol, SDS-PAGE of THP yielded a single band at 95 kilo daltons, suggesting that THP is a single peptide with intra-chain disulfide linkages.

Specificity was determined by THP ELISA test (MDBiosciences), results obtained showed that 1 mg of protein is equivalent to a 1 mg THP.

Endogenous proteins are rapidly cleared from the body and cannot be taken orally. In order to perform a successful treatment with a protein, frequent injections of the drug for a long period of time are often required.

A method to increase the efficiency of a therapeutic peptide or protein drug is based on chemical modification, achieved by means of chemical modification of the native molecules with polyethylene glycol (PEG), known as PEGylation.

Pegylated THP used in Assays showed in present application was prepared according the following protocols:

Protocol 1 (3.5 Mol of PEG/Mol of THP)

14.4 mg of THP was dissolved in 10 ml of distillate water; NaCl q.s. to 3.4% was added. The mixing was stirred and then maintained in standing by 2 hours at 2-8° C. The mixing was centrifuged and the precipitate recovered and washed once with NaCl 3.5%.

The precipitate obtained was dissolved in 10 ml of distillate water.

2.88 mg of PEG tresilate (Sigma-Aldrich) was added, the mixing was stirred two hours at room temperature.

NaCl q.s. to 3.5% was added and then maintained in standing by 1 hour.

The mixing was centrifuged and the precipitate conserved at −20° C.

Protocol 2 (7 Mols of PEG/Mol of THP)

3 vials of THP 09022010 (14.4 mg THP) were dissolved in 7.2 ml of distillate water.

The mixing obtained was dialyzed against 6 l of deionizer water at 4° C., and then it was stirred during 24 hours, with three changes of the bath.

On the next day the dialyzed was recovered, and the volume determined (17.4 ml).

It was added 3.76 mg of PEG tresilate and the mixing stirred by two hours at room temperature.

0.58 M of NaCl was added and the mixing was maintained in standing by two hours at 2-8° C.

The mixing was centrifuged and the precipitate conserved at −20° C.

Pharmaceutical compositions of pegylated Human Tamm Horsfall protein for parenteral administration were prepared dissolving the precipitate obtained by protocols 1 an 2 in distilled water in order to obtain a solution containing 1 mg/ml.

Pharmaceutical compositions containing native or pegylated THP described herein were administered to mammals suffering from or believed to be suffering from tumors. Also, it was administered to critical infected patients in order to increase their immune innate response.

In therapeutic applications for treating tumors, compositions are administered to a mammal in an amount sufficient to cause regression of the tumor, or at least to partially arrest the tumor growth and metastasis. An adequate amount to accomplish the abovementioned objectives is defined as a "therapeutically effective dose". The effective amount for those applications will depend on, for instance, the nature of the THP (specific activity, etc.), the way of administering it, the stage and severity of the tumors, the weight and general state of health of the mammal, and the judgment of the prescribing physician.

Single or multiple administrations of a peptide composition as a THP composition can be carried out with a dosing scheme being determined by the treating physician. In any event, the pharmaceutical formulations should provide a quantity of THP sufficient to effectively treat the mammal. Administration should begin at the first indication of undesirable cellular proliferation or shortly after diagnosis, and continue until symptoms are substantially abated and for a period thereafter. In well established cases of tumors, loading doses followed by maintenance doses may be required.

The pharmaceutical compositions for therapeutic treatment are intended for parenteral, topical, oral or local administration. The invention provides compositions for parenteral administration which comprise a solution of an anti-tumor THP dissolved or suspended in an acceptable carrier, preferably an aqueous carrier. A variety of aqueous carriers can be used, for instance, water, buffered water, 0.4% saline, 0.3% glycine, hyaluronic acid and the like. These compositions can be sterilized by conventional, well known sterilization techniques, or can be sterile filtered. The resulting aqueous solutions can be packaged for use as it is or lyophilized, the lyophilized preparation being combined with a sterile solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Other methods for preparing pharmaceutical compositions will be known or apparent to those skilled in the art and are described in more detail in, for example, Remington's Pharmaceutical Science, 19th ed., Mack Publishing Company, Easton, Pa. (1990), which is incorporated herein by reference.

Experimental Tests

A substantial body of experimental results is presented here to show that THP is capable of reducing development of tumors and infectious disease.

The experiments performed indicate that the administration of THP by subcutaneous route protect mice (CD1 strain) of T180 sarcoma cells development and from lethal peritonitis produced by *Salmonella enteritidis*.

THP was injected at two different dose, 15 or 30 mg/kg body weight, by subcutaneous route, in two injections at 48 hours interval. Additional doses were not injected because the rapid immune response of mice to human protein antigens could affect results.

Assay 1

Ascitic Sarcoma T 180 vs. THP Assay

Methods

Three groups of 6 adult male mice (CD1 strain in all cases) were used:

1) Control Group
2) THP (post-menopausal urine) group.
3) THP (pregnancy urine) group The assay was performed according the following scheme:

At Day 1 a) Body weight is registered in all the animals. 1 mL of Sarcoma 180 (87×10exp6 cells/mL) is injected by intra-peritoneal route.

b) Sub-cutaneous injection of 1 mL aqueous solution 1 mg/mL THP-HCG (Pilot Batch 09062010).

c) Sub-cutaneous injection of 1 mL aqueous solution 1 mg/mL THP-HMG (Pilot Batch 09062010).

At Day 3 and Day 4

Control of body weight was performed.

Results

The results are summarized in the following Tables and FIG. 1:

FIG. 1 shows the increase of body weights corresponding to Control Group 1) regarding the groups 2) and 3) respectively treated with THP-HCG and THP-HMG.

Conclusion of Assay 1:

As it can be appreciated, the values of body weight observed in groups 2) and 3) which were treated with THP, showed a decrease compared to the Control group 1); consequently it is considered that the animals in groups 2) and 3) suffered a decrease in body weights which could be associated to inhibition of tumor development performed by THP.

Assay 2

In order to confirm the conclusion obtained in Assay 1, Assay 2 was performed as follows:

Solid SARCOMA-180 vs. THP

| Results (grams of body weight). | | | | | | | | | |
|---|---|---|---|---|---|---|---|---|---|
| | Control | | | THP-HMG | | | THP-hCG | | |
| | | | | Day | | | | | |
| | 1 Sep. 28, 2011 | 3 Sep. 29, 2011 | 4 Sep. 30, 2011 | 1 Sep. 27, 2011 | 3 Sep. 29, 2011 | 4 Sep. 29, 2011 | 1 Sep. 27, 2011 | 3 Sep. 29, 2011 | 4 Sep. 30, 2011 |
| | 24.1 | 25.8 | 32.6 | 30.8 | 32.1 | 30.3 | 25.8 | 26.0 | 26.6 |
| | 26.5 | 26.2 | 29.3 | 24.0 | 23.1 | 24.1 | 25.9 | 27.0 | 32.0 |
| | 32.9 | 35.4 | 36.6 | 29.4 | 29.7 | 34.3 | 30.0 | 33.8 | 27.5 |
| | 27.0 | 29.4 | 37.6 | 27.0 | 29.0 | 26.4 | 29.8 | 32.2 | 29.4 |
| | 32.2 | 34.7 | 36.5 | 26.5 | 29.7 | 31.5 | 27.6 | 29.5 | 28.6 |
| | 27.2 | 34.2 | 27.7 | 24.5 | 26.2 | 28.1 | 27.0 | 27.3 | 31.9 |
| AVER. | 28.4 | 31.0 | 33.4 | 27.0 | 28.3 | 29.1 | 27.7 | 29.3 | 29.4 |

| Day | Control | THP-HMG | TNP-HCG |
|---|---|---|---|
| 1 | 28.4 | 27.0 | 27.7 |
| 3 | 31.0 | 28.3 | 29.3 |
| 4 | 33.4 | 29.1 | 29.4 |

| Student's t-test on Day 4 | |
|---|---|
| Control | THP-HMG |
| 32.6 | 30.3 |
| 29.3 | 24.1 |
| 36.6 | 34.3 |
| 37.6 | 26.4 |
| 36.5 | 31.5 |
| 27.7 | 28.1 |

| Two-sample t test assuming unequal variances | | |
|---|---|---|
| | Variable 1 | Variable 2 |
| Media | 33.3333333 | 29.35 |
| Variance | 17.4856667 | 4.943 |
| Observations | 6 | 6 |
| Hypothetical difference of mean | 0 | |
| Degrees of freedom | 8 | |
| Statistical t | 2.08611388 | |
| P(T <= t) one tail | 0.03522122 | |
| Critical value of t (one-tailed) | 1.85954803 | |
| P(T <= t) two tailes | 0.07044244 | |
| Critical value of t (two-tailed) | 2.30600413 | |

Methods:

Two groups of 6 adult male mice each were used:

Group 01 comprises Sarcoma group, wherein Sarcoma 180 was subcutaneously injected in six animals.

Group 02 comprises Sarcoma plus THP group, wherein six animals subcutaneously injected with Sarcoma 180 and injected with THP-HMG.

The assay was performed according the following scheme:

At Day 1 a) Mice were randomly distributed among the groups.

b) 0.5 mL of Sarcoma 180 cell suspension was subcutaneously injected (19×10exp6 cells/mL) on the right flank of the animals.

c) 1 mg of THP-HMG is injected to group 02: 1 mL of THP-HMG (Pilot Batch 09062010) by sub cutaneous route.

At Day 3

Group 02 receives a new dose of THP-HMG, 1 mg s.c. per animal.

At Day 5

All the animals are weighed and sacrificed. Tumors are dissected and weighed.

Results

The results are summarized in the following Tables and FIG. 2 corresponding to the dissected tumors:

Results

| I) Weight table | |
|---|---|
| Body weight | |
| Sarcoma (g) | Sarcoma-THP (g) |
| 35.7 | 32.8 |
| 32.5 | 34.8 |
| 35.2 | 31.3 |
| 35.5 | 33.8 |
| 35.6 | 32.3 |
| 34.8 | 29.0 |
| Aver. 34.9 | 32.3 |

| T test for two paired samples | | |
|---|---|---|
| | Variable 1 | Variable 2 |
| Media | 34.8833333 | 32.3333333 |
| Variance | 1.46966687 | 4.12666667 |
| Observations | 6 | 6 |
| Pearson correlation coefficient | −0.37898992 | |
| Hypothetical difference of mean | 0 | |
| Degrees of freedom | 5 | |
| Statitical t | 2.28643619 | |
| P(T <= t) one tail | 0.03548236 | |
| Critical value of t (one-tailed) | 2.01504837 | |
| P(T <= t) one tail | 0.07096471 | |
| Critical value of t (one-tailed) | 2.57058183 | |

| WEIGHT OF TUMOR | |
|---|---|
| Sarcoma (mg) | Sarcoma-THP (mg) |
| 197.5 | 106.8 |
| 401.0 | 108.5 |
| 363.7 | 160.0 |
| 296.3 | 288.9 |
| 216.0 | 106.9 |
| 509.4 | 408.8 |
| Aver. 330.7 | 196.7 |

| T test for paired two samples | | |
|---|---|---|
| | Variable 1 | Variable 2 |
| Media | 330.65 | 196.65 |
| Variance | 14009.293 | 15751.883 |
| Observations | 6 | 6 |
| Pearson correlation coefficient | 0.66770199 | |
| Hypothetical difference of means | 0 | |
| Degrees of freedom | 5 | |
| Statitical t | 5.29491506 | |
| P(T <= t) one tail | 0.01079808 | |
| Critical value of de t (one tail) | 2.01504837 | |
| P(T <= t) two tails | 0.02159616 | |
| Critical value of t (two tails) | 2.57058183 | |

Figure 2:
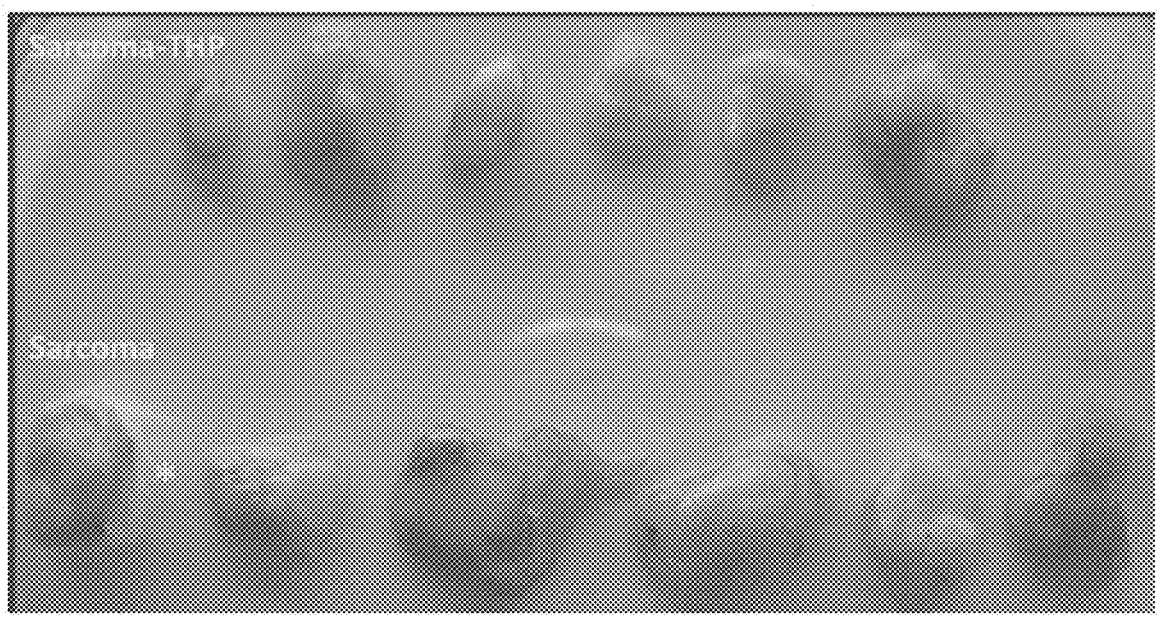
FIG. 2 shows the dissected tumors of ASSAY 2.

FIG. 2 shows the weight of dissected tumors wherein the tumor sizes of animals from group 01 (Sarcoma) results considerably larger than the group 02 (Sarcoma-THP).

Conclusion of Assay 2:

As it can be appreciated, the weight of tumors observed in group 02, which was treated with THP, are smaller than the ones from group 01; consequently it is considered that in group 02 the administration of THP inhibited tumor development and growth.

Assay 2 confirms that the decrease in body weights observed in Assay 1 is due to an inhibition of tumor development wherein the weight of tumors results smaller when THP is applied compared to a control group.

Assay 3

In order to evaluate if the administration of a foreign protein per-se could inhibit tumor development in mice, assay 3 was performed:

Sarcoma-180 vs. THP and Human Gamma Globulin

Methods:

Two groups with 6 albino adult male mice were used:

Group 1 corresponding to Sarcoma—hGamma globulina group (control group)

Group 2 corresponding to Sarcoma—THP group

The assay was performed according the following scheme:

At Day 1 a) 0.5 ml Sarcoma-180 cells suspension (40×10exp6 cells/ml) is injected in both groups by the subcutaneous route.

b) 1 mg of human Gamma-globulin is injected to animals of group 1: 1 ml saline with 1 mg/mL of human gamma globulin (Globulin-A 5000 mg) s.c.

c) 1 mg of THP-HMG is injected to group 2: 1 ml of aqueous solution containing 1 mg/ml of THP-HMG. (Pilot lot 09062010).

At Day 3

A new dose of THP-HMG and hGAMMA is injected to each group (idem day 1).

At Day 5

All the animals are weighed and sacrificed. Tumors are dissected and weighed.

Results

Figure 3:
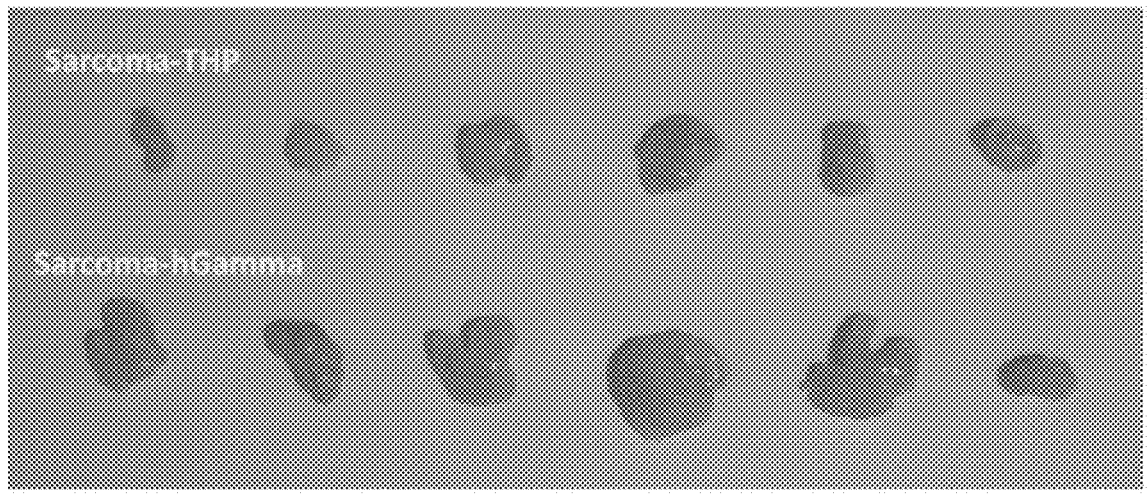
FIG. 3 shows the dissected tumors of ASSAY 3.

The results are summarized in the following Tables and FIG. 3 corresponding to the dissected tumors:

Results

| III) Table of weight | |
|---|---|
| Body weight | |
| Sarcoma-hGamma (g) | Sarcoma-THP (g) |
| 30.7 | 28.7 |
| 30.5 | 27.6 |
| 33.5 | 27.9 |
| 27.2 | 25.0 |
| 33.8 | 31.9 |
| 26.2 | 28.2 |
| Aver. 30.3 | 28.2 |

| Student T test for two paired samples. | | |
|---|---|---|
| | Variable 1 | Variable 2 |
| Media | 30.31558887 | 28.21668667 |
| Variance | 9.821666667 | 4.925665667 |
| Observations | 6 | 6 |
| Pearson correlation coefficient | 0.632262178 | |
| Hypothetical difference of mean | 0 | |
| Degrees of freedom | 5 | |
| Statitical t | 2.108450738 | |
| P(T <= t) one tail | 0.044398089 | |
| Critical value of t (one tail) | 2.015048372 | |
| P(T <= t) two tails | 0.088796178 | |
| Critical value of t (two tails) | 2.570581835 | |

| TUMOR WEIGHT | |
|---|---|
| Sarcoma-hGamma (mg) | Sarcoma-THP (mg) |
| 277.4 | 76.9 |
| 334.0 | 103.3 |
| 159.1 | 214.2 |
| 345.7 | 201.0 |
| 602.2 | 203.2 |
| 434.6 | 86.4 |
| Aver. 358.8 | 147.5 |

III) Table of weight

Student T test for two paired samples.

|  | Variable 1 | Variable 2 |
|---|---|---|
| Mean | 358.8333333 | 147.5 |
| Variance | 22456.37867 | 4216.968 |
| Observations | 6 | 6 |
| Pearson correlation coefficient | 0.035928672 | |
| Hypothetical difference of mean | 0 | |
| Degrees of freedom | 5 | |
| Statistical t | 3.211985079 | |
| P(T <= t) one tail | 0.011838127 | |
| Critical value of t (one tail) | 2.015048372 | |
| P(T <= t) two tails | 0.023676253 | |
| Critical value of t (two tails) | 2.570581835 | |

Conclusion of Assay 3:

As it can be appreciated, the administration of a foreign protein as human Gamma-globulin does not inhibit the tumor development and growth as can be seen from the body and tumor weight results, compared to the same values obtained from the group where THP was applied.

Assay 4

In order to evaluate the efficacy in tumor growth inhibition of a THP derivative, as Pegylated THP, Assay 4 was performed.

Pegylated THP Antitumoral Activity

Method

Two groups with 6 adult male mice each were used:
Group 1 corresponding to Sarcoma group
Group 2 corresponding to Sarcoma—THP-PEG group
The assay was performed according the following scheme:

At Day 1 a) 0.5 ml of Sarcoma-180 cells suspension (30×10exp6 cells/ml) were injected in both groups on the right flank of the animals.

b) 1 mg THP-PEG dissolved in 1 mL aqueous solution is injected on the left flank of each animal from Group 2.

Day 3

The weight of the animals was registered.

Group 2 receives a second dose (idem to Day 1 b) of THP-HMG-PEG: subcutaneous injection of 1 ml of an aqueous solution containing 1 mg/ml of THP-HMG-PEG on the left flank of the animal.

Day 6

All the animals are weighed and sacrificed, tumors are dissected and weighed.

Results

The results are summarized in the following Tables:

Results:

V) Tables of weight

| | Sarcoma (Control) | Sarcoma + THP-PEG |
|---|---|---|
| | CORPORAL WEIGHT ON DAY 6(g) | |
| | 33.1 | 30.6 |
| | 29.6 | 29.6 |
| | 28.3 | 28.3 |
| | 32.6 | 32.6 |
| | 31.4 | 31.4 |
| | 28.2 | 28.2 |
| Aver. | 30.5 | 30.1 |

V) Tables of weight

| | TUMOR WEIGHT(mg) | |
|---|---|---|
| | 307.3 | 59.4 |
| | 104.0 | 44.9 |
| | 276.6 | 154.1 |
| | 158.4 | 87.2 |
| | 118.9 | 67.9 |
| | 107.9 | 89.7 |
| Prom. | 178.85 | 83.87 |

Student t test for paired samples.

|  | Variable 1 | Variable 2 |
|---|---|---|
| Media | 178.85 | 83.86666667 |
| Variance | 8140.619 | 1469.962667 |
| Observations | 6 | 6 |
| Pearson correlation coefficient | 0.411325076 | |
| Hypothetical difference of mean | 0 | |
| Degrees of freedom | 5 | |
| Statistical t | 2.828750208 | |
| P(T <= t) one tail | 0.018364323 | |
| Critical value of t (one tail) | 2.015048372 | |
| P(T <= t) two tails | 0.036728645 | |
| Critical value of t (two tails) | 2.570581835 | |

Conclusion of Assay 4:

As it can be appreciated, the tumor weights obtained at Day 6 were considerably lower for the group of animals treated with THP-PEG compared to the group of animals not treated, which demonstrates that THP-PEG produces an inhibition of tumor development and growth as well as native THP.

Assay 5

This assay had the objective of evaluating the efficacy of the treatment with THP on previously developed tumors.

THP Antitumoral Activity of THP on Previously Developed Tumors

Methods:

Three groups of 6 adult male mice were used:
Group 1 Sarcoma (Day 3 tumor development)
Group 2 Sarcoma (control group)
Group 3 Sarcoma THP The assay was performed according the following scheme:

At Day 1 a) 0.5 ml sarcoma 180 cells suspension (28×10exp6 cells/ml) was injected on the right flank of each animal, subcutaneously.

At Day 3 b) Group 1, mice are sacrificed, tumors are dissected and weighted, to establish the development degree of tumors at this stage.

1 mg of THP-HMG is injected to Group 2: 1 ml of aqueous solution containing 1 mg/ml of THP is injected on the left flank of each animal, subcutaneously.

At Day 5

1 mg THP-HMG is administered to Group 2 (idem Day 3).

At Day 7

Mice are weighed, sacrificed, and the tumors dissected and weighed.

Results

The results are summarized in the following Tables and FIG. 4, corresponding to the mean weight of tumors in Groups 2 and 3:

Results

I) Table of tumor weight

| | Tumor weight (mg) | | |
|---|---|---|---|
| | Group 1<br>Day 4<br>Sarcoma | Group 2<br>Day 7<br>Sarcoma-THP | Group 3<br>Day 7<br>Sarcoma |
| | 29.4 | 60.9 | 182.9 |
| | 48.7 | 53.7 | 209.1 |
| | 30.0 | 47.4 | 215.8 |
| | 18.1 | 54.6 | 105.3 |
| | 33.1 | 38.3 | 128.9 |
| | 34.4 | 8.6 | 110.6 |
| Aver. | 32.3 | 43.9 | 158.8 |

Statistical;

Student T test. Group 1 versus Group 2: p 0.26.

Student T test. Group 2 versus Group 3: p 0.0019.

II) Body weight on day 7

| | Body weight (Day 7) | |
|---|---|---|
| | Group 2<br>(Sarcoma-THP) | Group 3<br>(Sarcoma) |
| | 33.5 | 32.1 |
| | 34.9 | 34.6 |
| | 34.4 | 40.0 |
| | 38.5 | 32.1 |
| | 34.1 | 37.9 |
| | 39.0 | 38.9 |
| Aver. | 35.7 | 35.9 |

Figure 4:
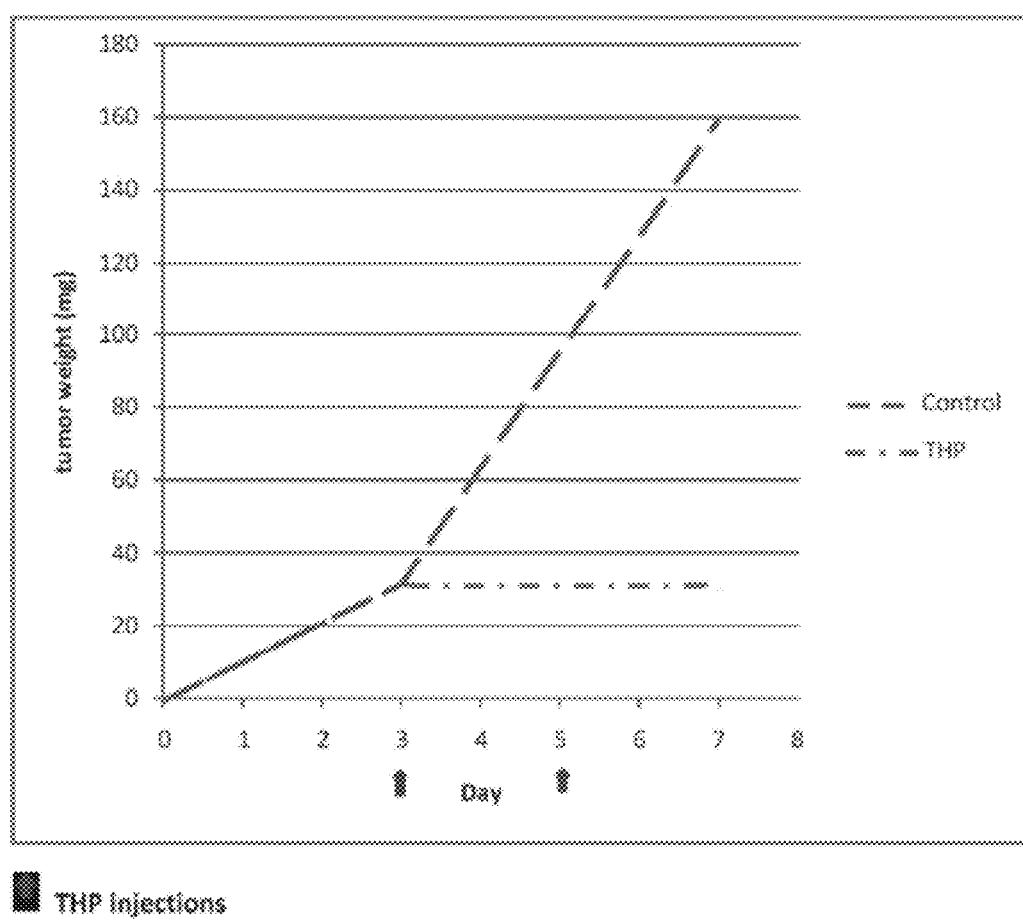
FIG. 4 is a graph depicting tumor weight vs. Day for Control and THP showing mean weight of tumors in Groups 2 and 3 in ASSAY 5.

FIG. 4 shows mean weight of tumors in Group 2 and 3.

In the graph can be seen that at day 7, the average weight of the tumors in the animals to which THP was injected was considerably lower than the weight of the tumors from animals which were not treated with THP (control group).

Conclusion of Assay 5:

As it can be appreciated, the treatment with THP on mice which had previously developed tumors inhibited tumor development and growth in comparison with animals not treated.

Assay 6

This assay showed an Anti-infections protection action obtained from the treatment with THP Anti-Infectious Protection by THP.

Method

Lethal peritonitis in mice inoculated with *Salmonella enteritidis* plus ovine hemoglobin is used as challenge.

The assay was performed according the following scheme:

At Day 1: THP 0.1 mg, 0.5 mg, 1 mg and 5 mg is injected subcutaneously to groups of adult male mice.

A control group is injected with excipient.

At Day 2: All the animals received by intra-peritoneal route 1 mL of a *Salmonella enteritidis* suspension (24 hours broth) mixed with an equal volume of 10 g/100 ml ovine hemoglobin solution.

The mortality caused by peritonitis in mice is observed in the following Table:

Mortality by Peritonitis in Mice

Observation time: 10 hours after *S. enteritidis* inoculation.

| Treatment | Live | Deaths | Percentage of death animals. |
|---|---|---|---|
| Control | 1 | 6 | 86 |
| THP 0.1 mg | 0 | 5 | 100 |
| THP 0.5 mg | 1 | 4 | 80 |
| THP 1 mg | 5 | 0 | 0 |
| THP 5 mg | 5 | 0 | 0 |

Fisher's Exact Test

| | Peritonitis by *S. enteritidis* in mice | | |
|---|---|---|---|
| | live | deaths | total |
| control | 1 | 6 | 7 |
| THP | 5 | 0 | 5 |
| total | 6 | 6 | 12 |
| probability | 0.0000015 | | |

Conclusion of Assay 6:

As it can be appreciated, the treatment with THP in doses higher than 1 mg decreases the mortality by peritonitis when *Salmonella enteritidis* is inoculated in mice. THP increases the defense barriers in mice against *Salmonella enteritidis*.

Report of Antitumor Effect of THP

In order to confirm the conclusions of Assay 1-6, specially the results from Assay 5 (efficacy of THP on previously developed tumors) and evaluate the antitumor action of THP against different tumor cell lines in different species of mice, in vivo studies were performed considering the following paper references:

1. Guide for the Care and Use of Laboratory Animals. Washington. Institute of Laboratory Animal Resources, Commission on Life Sciences National Research Council. 1996. DC: National Academy Press.
2. Tao K, Fang M, Alroy J, Sahagian G G. Imagable 4T1 model for the study of late stage breast cancer. BMC Cancer 2008; 8:228.
3. Brattain M G, Strobel-Stevens J, Fine D, Webb M, Sarrif A M. Establishment of mouse colonic carcinoma cell lines with different metastatic properties. Cancer Res 1980; 40:2142-46.
4. Fidler I J, Kripke M L. Metastasis results from preexisting variant cells within a malignant tumor. Science 1977; 197:893-95.
5. Leng H M, Albrecht C F, Kidson S H, Folb P I. Erythropoietin production in anemia associated with experimental cancer. Exp Hematol 1999; 27:806-10.

The assays were performed as follows:

Materials and Methods

Reagents: Human Tamm-Horsfall protein (THP, Lot: 26062012; 0.9 mg/ml) dissolved in 40 mM TRIS pH=8, was used. Dilutions were performed in sterile apirogen water.

Cell Culture: 4T1 mouse mammary tumor cells, CT26 mouse colon carcinoma, and B16 melanoma cell lines were obtained from the American Type Culture Collection (Manassas, Va.). 4T1 and CT26 were cultured in RPMI 1640 medium (Life Technologies, Grand Island, N.Y.), and supplemented with 2 mM glutamine and 10% fetal calf serum (FCS, Gen, Buenos Aires, Argentina). B16 cells were cultured in RPMI 1640 medium high glucose, and supplemented with non-essential aminoacids, 2 mM glutamine and 10% FCS. All cell types were cultured at 37° C. in a humidified incubator containing 5% $CO_2$.

In vivo studies: Experiments were carried out in virgin female BALB/c mice (8-9 weeks of age), raised at the Institute of Biology and Experimental Medicine of Buenos Aires (for 4T1 and CT26 cell lines experiments) or in virgin female C57BL mice (8-9 weeks of age) obtained from National University of La Plata (Buenos Aires, Argentina, for B16 experiments), and under pathogen free conditions using HEPA filter hoods. The mice were group housed under conditions of constant photoperiod (12 hours light: 12 hours dark) with ad libitum access to food and water in groups of 4-5 in plastic cages vented with polyester fiber filter covers. Each animal was earmarked and followed individually throughout the experiments. All animal studies were conducted in accordance with the highest standards of animal care as outlined by the National Institutes of Health's Guide for the Care and Use of Laboratory Animals (1).

Each mouse was inoculated subcutaneously (s.c.) in the right flank with $1 \times 10^5$, $3 \times 10^5$, $2.5 \times 10^5$ for the cell lines 4T1, CT26 and B16 respectively in a total volume of 0.1 ml serum-free medium. As tumors became established (mean starting tumor volume, ~100 $mm^3$), mice were randomized to different groups (day 1) and were s.c. injected in the left flank with 150 microliters of different doses of THP. Mice received three doses in total, one every other day starting at day 1. At day 7, mice were sacrificed.

4T1 Cells.

Mice were randomized in five groups (n=10) that received the following treatments: (a) Control (TRIS 4 mM pH=8) (b) 187 micrograms/kg body weight/dose, (c) 375 micrograms/kg body weight/dose, (d) 750 micrograms/kg body weight/dose and (e) 1500 micrograms/kg body weight/dose.

CT26 Cells.

Mice were randomized in four groups that received the following treatments: (a) Control (TRIS 4 mM pH=8), n=5 (b) 375 micrograms/kg body weight/dose, n=4 (c) 750 micrograms/kg body weight/dose, n=4 and (d) 1500 micrograms/kg body weight/dose, n=4.

B16 Cells.

Mice were randomized in four groups (n=8) that received the following treatments: (a) Control (TRIS 4 mM pH=8) (b) 375 micrograms/kg body weight/dose, (c) 750 micrograms/kg body weight/dose and (d) 1500 micrograms/kg body weight/dose.

In all experiments tumors were measured three times a week using digital caliper and their volumes calculated using a standard formula: ($width^2 \times length$)/2. Tumor growth rates were determined as the slopes of growth curves estimated by volume measure. Body weights were measured weekly. The percentage of tumor growth inhibition was calculated by dividing the mean tumor volume or weight of the THP-treated group by the mean tumor volume or weight of control groups, subtracting the resulting value from 1, and multiplying it by 100. At terminal sacrifice, liver, spleen, lungs and kidneys were removed and tumors were harvested and weight. Spleen was also weighted. All the organs and tumors tissues were fixed overnight in 10% formalin then transferred to 70% ethanol. Four micrometer-thick, paraffin-embedded tissue sections were stained with hematoxylin and eosin by standard procedures. Blood from each mouse was evaluated of hematological parameters using a Coulter Counter.

Statistical analysis: For comparison of relative tumor weights between multiple groups of animals, ordinary ANOVA followed by Tukey-Kramer multiple Comparison post ANOVA analysis was performed. Probability values (P) less than 0.05 were considered statistically significant.

Results

To examine the in vivo antitumor efficacy of THP, different tumor models were used.

Figure 5:
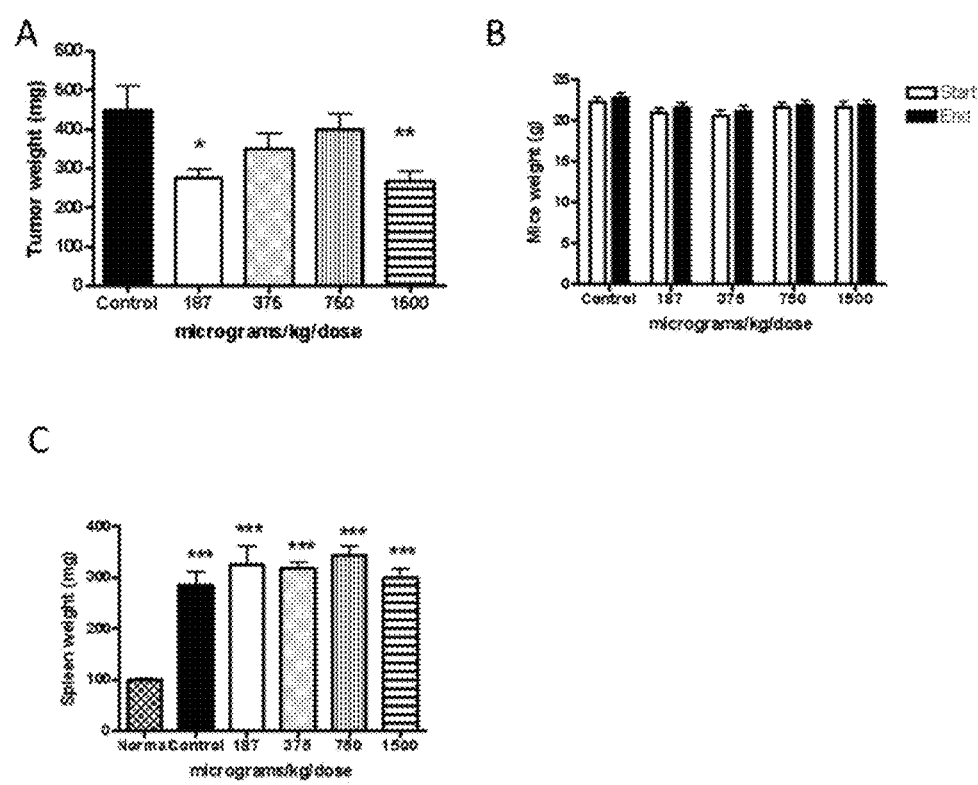
FIG. 5 corresponds to graphs showing the effect of THP administration on mice bearings 4T1 breast cancer of the Report of antitumor effect of THP. When tumors reached $128.6 \pm 7.9$ mm$^3$ (day 1) THP was administrated s.c. at 187, 375, 750 and 1500 mg/kg/day three times every other day, and on day 7 animals were sacrificed. (A) Tumor weight. *$P<0.05$, $P<0.01$. (B) Animal weight at the start (day 1) and at the end (day 7) of the experiment. (C) Spleen weight *$P<0.001$. Data are shown as mean±SEM (n=10).
Figure 6:
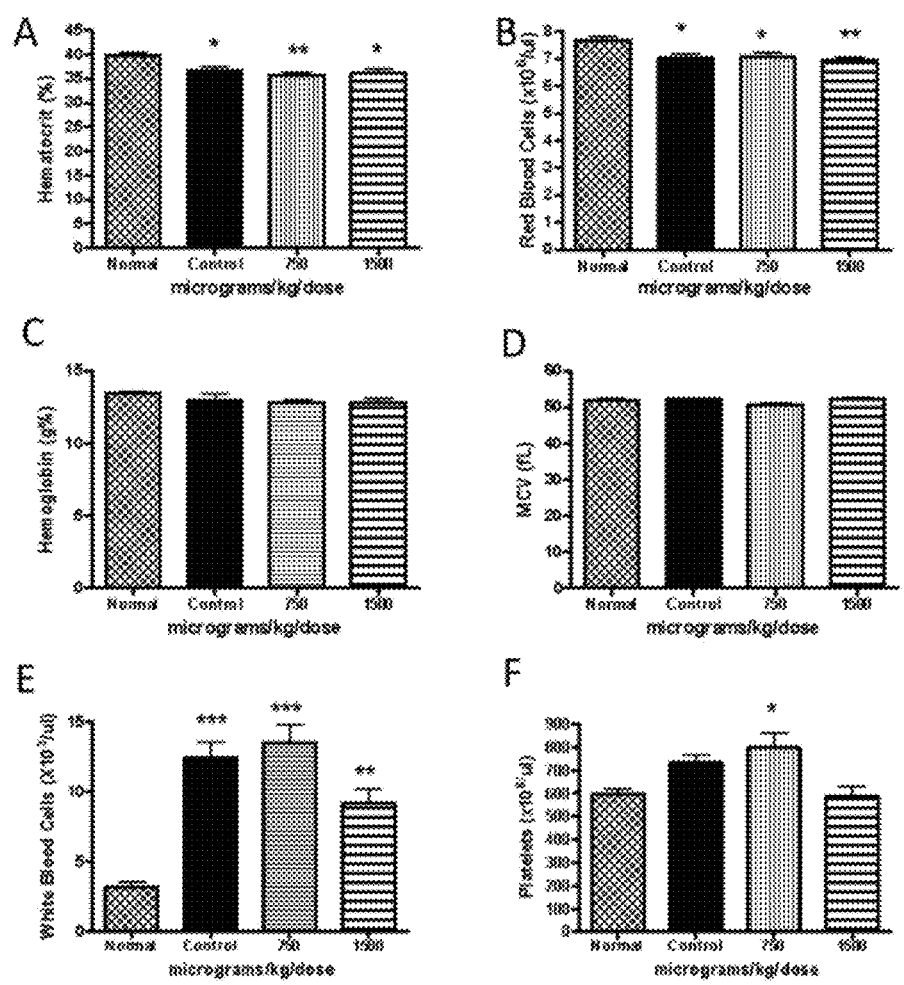
FIG. 6 corresponds to graphs showing the effect of THP administration on hematological indexes in mice bearing 4T1 breast cancer of the Report of antitumor effect of THP. At the end of the experiment (day 7 of treatment) (A) hematrocrit, (B) red blood cells, (C) hemoglobin, (D) mean corpuscular volume (MCV), (E) white blood cells, and (F) platelets count were determined in peripheral blood of mice. Normal healthy animals (n=9), mice with tumors treated with vehicle (control) or with different dosis of THP (n=10) were used. *$P<0.05$, $P<0.01$ and *$P<0.001$ vs. normal mice. Data are shown as mean±SEM.

4T1 Cells:

First, we studied THP effect on 4T1 breast cancer growth (2). BALB/c mice bearing established subcutaneous 4T1 tumor (mean tumor volume, 128.6±7.9 $mm^3$) were treated s.c. for 7 days with THP at 187, 375, 750 or 1500 micrograms/kg every other day or with vehicle. As shown in FIG. 5A, treatment of mice with 187 and 1500 mg/kg of THP significantly inhibited 4T1 tumor growth by 38% and 40%, respectively (Table 1) at day 7, relative to vehicle-treated controls (P<0.05 and P<0.01 respectively). Tumor growth rates, determined as the slopes of growth curves obtained during THP or vehicle treatment, were lower in all THP-treated groups, compared with vehicle-treated animals (Table 1). Importantly, mice appeared to tolerate treatment with THP without overt signs of toxicity, without significant variation of body weight compared to vehicle-treated controls (FIG. 5B). The typical splenomegalia derived from 4T1 tumor (2) was observed in all mice with tumors respect to normal mice (FIG. 5C). This was accompanied by an increase in white blood cells as it was already reported (2) (FIG. 6E). THP administration did not modify either spleen weight (FIG. 5C) nor white blood cells count (FIG. 6E). A small decline in hematocrit and in red blood cells was observed in all 4T1 bearing mice (FIGS. 6A and B, respectively). No changes occurred in the mean corpuscular volume (MCV) and hemoglobin concentration values (FIGS. 6C and D, respectively). An increase in platelet count was observed in mice treated with the dose of 750 micrograms/kg (FIG. 6F).

Figure 7:
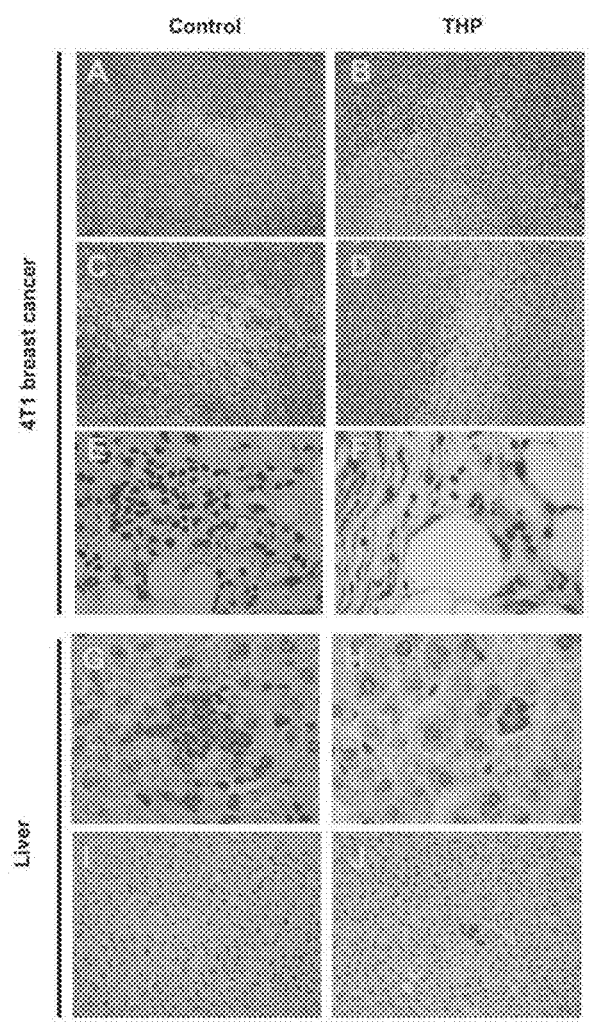
FIG. 7 corresponds to graphs showing histological analysis of 4T1 tumors and liver from mice treated with THP of the Report of antitumor effect of THP. At the end of the experiment (day 7 of treatment), tumor and liver were fixed and embedded in paraffin as described in Material and Methods section. Tissue section of tumors from control (A, C and E) and THP-treated mice (B, D and F). Highly necrotic tumor and extensive fibrotic areas from THP-treated mice are shown (B and D) in comparison to control mice (A and C). Inflammatory infiltrate is more abundant in control mice vs. THP-treated mice (E vs. F). Liver metastasis are smaller in THP vs. control mice (H vs. G). Liver cytotoxicity is present in control mice (I). (A-D) H&E×50; (E and F) H&E×400; (G and H) H&E×200; (I and J) H&E×50.

To study histopathological features, tumors excised at day 7 of treatment were evaluated by hematoxylin-eosin (H&E) staining. FIG. 7A-F shows representative sections of tumors from control and from THP 1500 mg/kg/dose experimental groups. Extensive necrotic areas (30-50% of tumor mass) were found in tumors grown in mice treated with THP (FIG. 7B). On the other hand, control mice showed focal necrosis (5-20%, FIG. 7A). A significant fibrotic area was observed in mice treated with THP (15-25%, FIG. 7D) meanwhile fibrosis was scarcely seen in control mice (5%, FIG. 7C). Peritumoral infiltration of inflammatory cells (lymphocytes, plasmocytes, mastocytes and some neutrophils) were more abundant in control in comparison to THP-treated mice (FIG. 7E and FIG. 7F, respectively). 4T1 tumors grown in control and THP-treated mice exhibit anaplasia (nuclear grade=3), high mitotic index (mitotic grade=3) and poor differentiation (histological index=3) (FIG. 7A-F). Histological examination of liver revealed the presence of localized metastases in the sinusoid spaces, with spherical appearance (FIG. 7G and FIG. 7H). THP-treated animals showed metastasis of smaller size (smaller number of tumor cell in the metastasis) than control (FIG. 7H and FIG. 7G respectively) and a normal histological features (FIG. 7J). On the other hand, liver from control animals showed important hepatocyte cytoxicity (FIG. 7I). Renal morphology and structure showed a mild-to-moderate cloudy degeneration of renal cortical tubular epithelium in animals under THP treatment and a moderate cloudy degeneration of renal cortical tubular epithelium in control animals. Pulmonary congestion and splenomegalia with extramedullary hematopoiesis were observed in control and THP-treated mice.

The effect of s.c. administration of THP on the growth of the tumor cell line 4T1 is summarized in the following Table 1:

TABLE 1

Effect of s.c. administration of THP on 4T1 tumor growth

| Treatment THP (μg/kg/dose) | Mean tumor weight (g) ± SEM | Mean Growth Rate ± SEM (mm³/day) | % growth inhibition |
|---|---|---|---|
| Control | 449.7 ± 60.3 | 39.9 ± 6.0 | |
| 187 | 277.3 ± 21.0* | 24.9 ± 5.5 | 38 |
| 375 | 349.3 ± 38.5 | 26.8 ± 5.9 | 22 |
| 750 | 398.5 ± 39.9 | 26.3 ± 8.5 | 11 |
| 1500 | 267.7 ± 23.5** | 32.4 ± 6.6 | 40 |

*P < 0.05;
**P < 0.01 vs control

When tumors reached 128.6±7.9 mm³, mice were treated as described in Materials and Methods. Each group contained 10 mice. Growth rate between day 1 of treatment and day 7, end of the experiment, was calculated as the slopes of growth curves. At the end of the experiment, tumor weight and percentage of growth inhibition in tumors from THP-treated mice with respect to vehicle-treated animals (control) was calculated as described in Materials and Methods.

Figure 9:
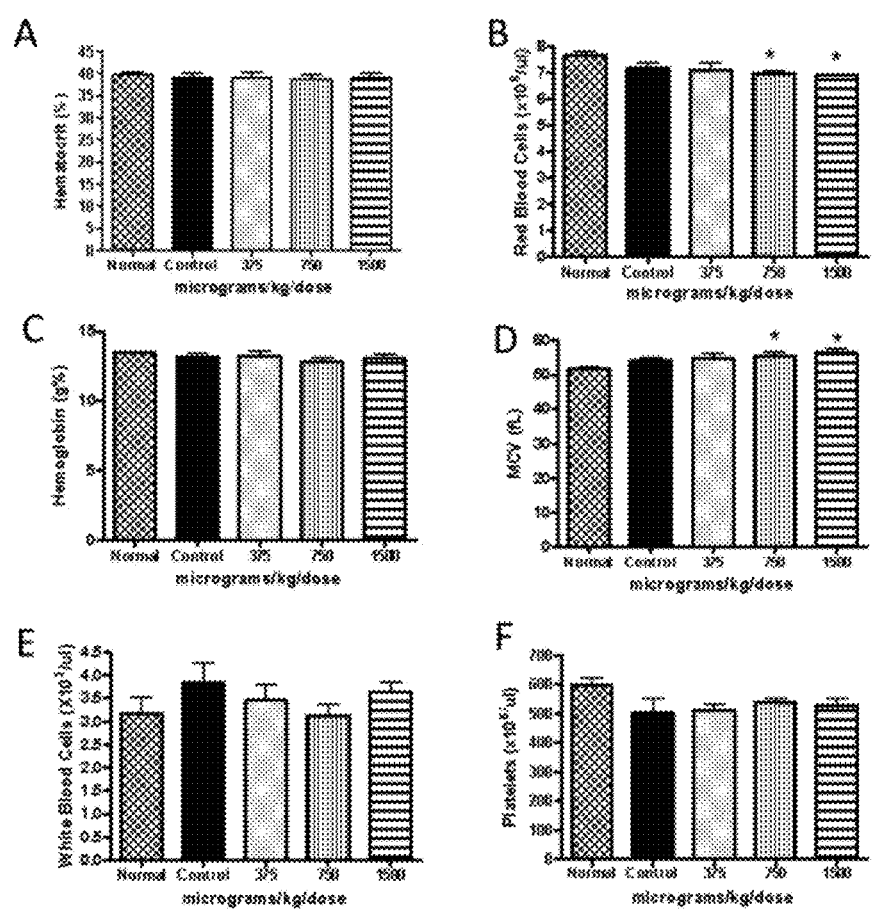
FIG. 9 corresponds to graphs showing the effect of THP administration on hematological indexes in mice bearing CT26 colon cancer of the Report of antitumor effect of THP. At the end of the experiment (day 7 of treatment) (A) hematrocrit, (B) red blood cells, (C) hemoglobin, (D) mean corpuscular volume (MCV), (E) white blood cells, and (F) platelets count were determined in peripheral blood of mice. Normal healthy animals (n=9), mice with tumors treated with vehicle (control, n=5) or with different doses of THP (n=4) were used. *P<0.05 vs. normal mice. Data are shown as mean±SEM.
Figure 10:
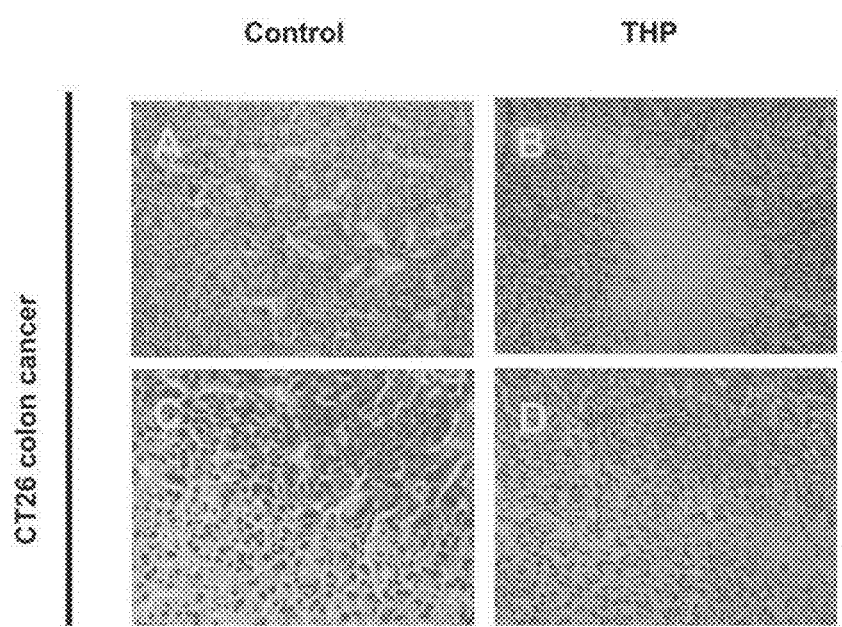
FIG. 10 corresponds to graphs showing histological analysis of CT26 tumors from mice treated with THP of the Report of antitumor effect of THP. At the end of the experiment (day 7 of treatment), tumors were fixed and embedded in paraffin as described in Material and Methods section. Tissue section of tumors from control (A and C) and THP-treated mice (B and D). Necrotic tumor areas from THP-treated mice are shown (B and D) in comparison to control mice (A and C). Intratumor vascularization is evident (A-D), H&E×100.

CT26 Cells:

Second, we studied THP effect on CT26 colon cancer growth (3). BALB/c mice bearing established subcutaneous CT26 tumor (mean tumor volume, 88.6±12.0 mm³) were treated s.c. for 7 days with THP at 375, 750 or 1500 micrograms/kg every other day or with vehicle. As shown in FIG. 8A, treatment of mice with 1500 mg/kg of THP significantly inhibited CT26 tumor growth by 39% (Table 2) at day 7, relative to vehicle-treated controls (P<0.05). Tumor growth rates were lower in 750 and 1500 mg/kg of THP-treated group compare with vehicle-treated animals (Table 2). Importantly, mice appeared to tolerate treatment with THP without overt signs of toxicity, with a significant increase of body weight in all groups, including vehicle-treated controls (FIG. 8B), and with splenomegalia in all groups bearing CT26 tumor respect to normal mice (FIG. 8C). The hematological indexes revealed no changes in hematocrit, hemoglobin, white blood cells and platelets in normal animals in comparison to CT26-bearing mice treated or not with THP (FIGS. 9A, C, E and F). However, a decrease in red blood cells and an increase of MCV were observed in mice treated with 750 and 1500 micrograms/kg of THP (FIGS. 9B and 9D, respectively).

To study histopathological features, tumors excised at day 7 of treatment were evaluated by hematoxylin-eosin (H&E) staining. FIG. 10A-D shows representative sections of tumors from control and from THP 1500 mg/kg/dose experimental groups. Necrotic areas (15-20% of tumor mass) were found in tumors grown in mice treated with THP (FIG. 10B and FIG. 10D) and control mice showed minimal necrotic areas (5-10%, FIG. 10C). CT26 tumors grown in control and THP-treated mice exhibit anaplasia (nuclear grade=3), high mitotic index (mitotic grade=3) and poor differentiation (histological index=3) and show extensive intratumor vascularization (FIG. 10A-D). Renal morphology and structure showed a mild cloudy degeneration of renal cortical tubular epithelium in animals under THP treatment and a moderate cloudy degeneration of renal cortical tubular epithelium in control animals.

Pulmonary congestion and splenomegalia with extramedullary hematopoiesis were observed in control and THP-treated mice.

The effect of s.c. administration of THP on the growth of the tumor cell line CT26 is summarized in the following Table 2:

TABLE 2

Effect of s.c. administration of THP on CT26 tumor growth

| Treatment THP (μg/kg/dose) | Mean tumor volume (mm³) ± SEM | Mean Growth Rate ± SEM (mm³/day) | % growth inhibition |
|---|---|---|---|
| Control | 502.5 ± 57.4 | 68.0 ± 9.6 | |
| 375 | 502.1 ± 188 | 71.3 ± 21.3 | 0 |
| 750 | 378.7 ± 68.8 | 50.3 ± 10.2 | 25 |
| 1500 | 307.7 ± 6.9* | 39.3 ± 6.4 | 39 |

*P < 0.05

When tumors reached 88.6±12.0 mm³, mice were treated as described in Materials and Methods. Control group contained 5 mice and THP-treated group, 4 mice. Growth rate between day 1 of treatment and day 7, end of the experiment, was calculated as the slopes of growth curves. At the end of the experiment, tumor volume and percentage of growth inhibition in tumors from THP-treated mice with respect to vehicle-treated animals (control) was calculated as described in Materials and Methods.

Figure 11:
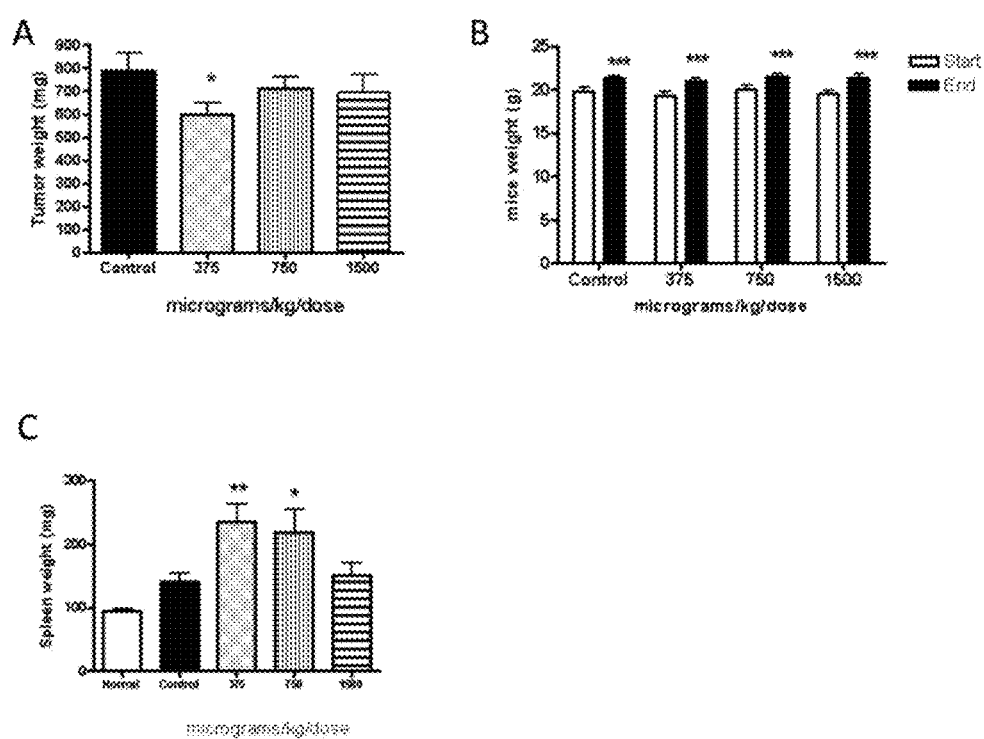
FIG. 11 corresponds to graphs showing the effect of THP administration on mice bearing B16 melanoma of the Report of antitumor effect of THP. When tumors reached $180.4 \pm 13.2$ mm$^3$ (day 1) THP was administrated s.c. at 375, 750 and 1500 mg/kg/day three times every other day, and on day 7 animals were sacrificed. (A) Tumor weight. *P<0.05. (B) Animal weight at the start (day 1) and at the end (day 7) of the experiment. ***P<0.001. (C) Spleen weight *P<0.05, **P<0.01. Data are shown as mean±SEM (n=8).

B16 Cells:

Finally, we studied THP effect on B16 melanoma growth (4). C57BL mice bearing established subcutaneous B16 tumor (mean tumor volume, 180.4±13.2 mm³) were treated s.c. for 7 days with THP at 375, 750 or 1500 micrograms/kg every other day or with vehicle. As shown in FIG. 11A, treatment of mice with 375 mg/kg of THP significantly inhibited B-16 tumor growth by 24% (Table 3) at day 7, relative to vehicle-treated controls (P<0.05). Tumor growth rate was lower in 375 mg/kg of THP-treated group compare with vehicle-treated animals (Table 3). Importantly, mice appeared to tolerate treatment with THP without overt signs of toxicity, with a significant increase of body weight in all groups, including vehicle-treated controls (FIG. 11B), and with significant splenomegalia in 375 and 750 mg/kg of THP-treated groups respect to controls and normal group (FIG. 11C).

Figure 12:
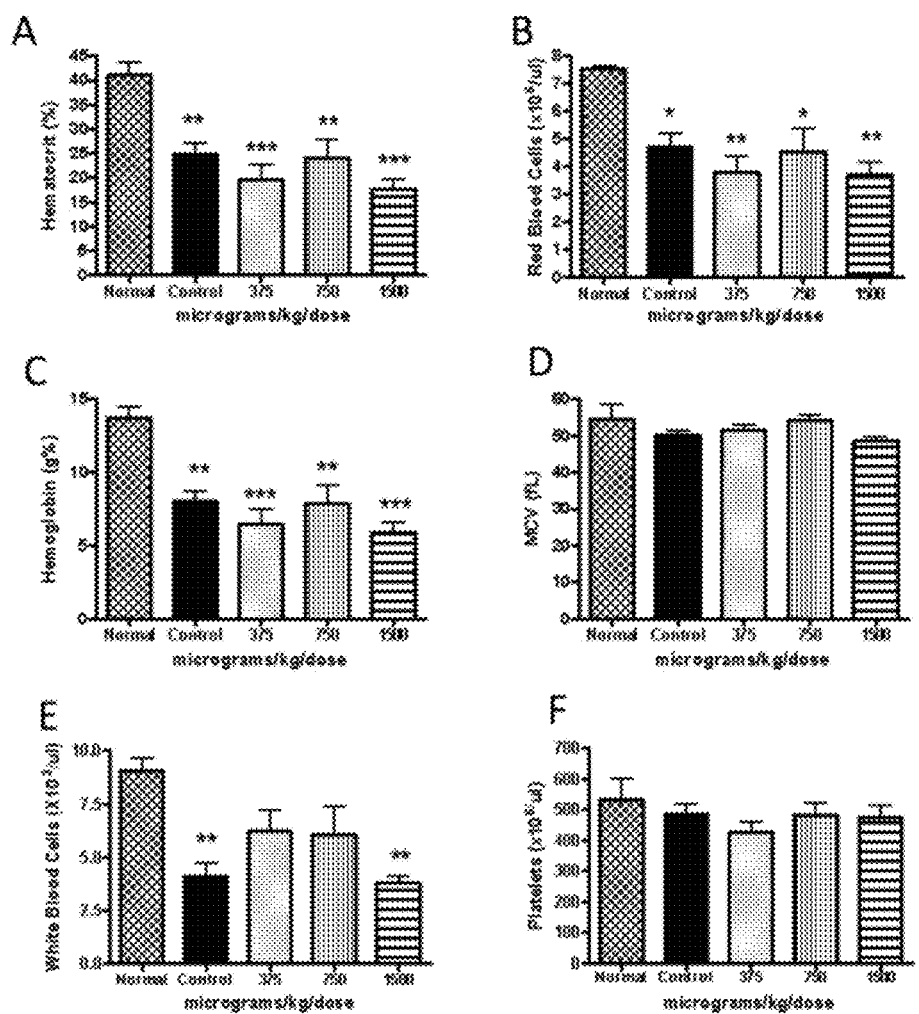
FIG. 12 corresponds to graphs showing the effect of THP administration on hematological indexes in mice bearing B16 melanoma of the Report of antitumor effect of THP. At the end of the experiment (day 7 of treatment) (A) hematrocrit, (B) red blood cells, (C) hemoglobin, (D) mean corpuscular volume (MCV), (E) white blood cells, and (F) platelets count were determined in peripheral blood of mice. Normal healthy animals (n=6), mice with tumors treated with vehicle (control) or with different dosis of THP (n=8) were used. *P<0.05, P<0.01 and *P<0.001 vs. normal mice. Data are shown as mean±SEM.

A decline in erythropoietic indices accompanied B16 tumor growth as it was already described (5). A decrease in hematocrit, red blood cells and hemoglobin was evident in all mice bearing B16 tumor and THP treatment did not modify these parameters (FIGS. 12A, B and C, respectively). The MCV was normal in all groups. White blood cells count decreased in animals bearing B16 tumor treated with vehicle (control) or treated with 1500 micrograns/kg of THP. The treatment with THP 375 and 750 micrograns/kg increased with bood cells number to levels similar con normal mice (FIG. 12E). No changes in platelets count was observed among all the studied groups (FIG. 12F).

Figure 13:
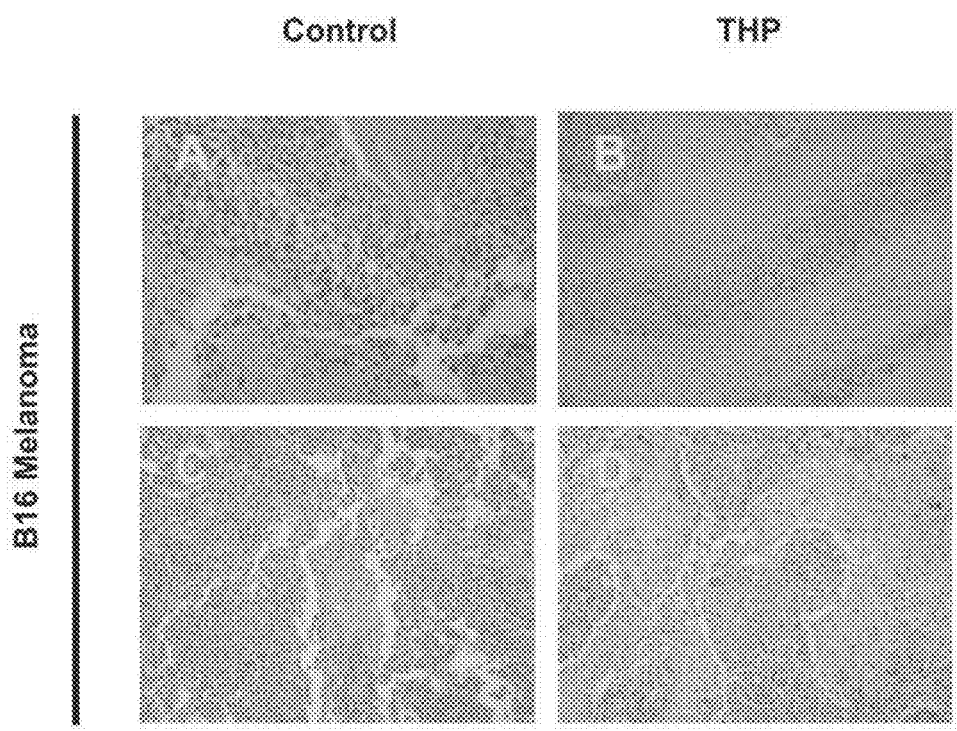
FIG. 13 corresponds to graphs showing histological analysis of B16 tumors from mice treated with THP of the Report of antitumor effect of THP. At the end of the experiment (day 7 of treatment), tumors were fixed and embedded in paraffin as described in Material and Methods section. Tissue section of tumors from control (A and C) and THP-treated mice (B and D). Highly necrotic tumor and extensive fibrotic areas from THP-treated mice are shown (B and D) in comparison to control mice (A and C). Intratumor vascularization is evident (A-D), H&E×50.

To study histopathological features, tumors excised at day 7 of treatment were evaluated by hematoxylin-eosin (H&E) staining. FIG. 13 A-D shows representative sections of tumors from control and from THP 375 mg/kg/dose experimental groups. Extensive necrotic areas (40-55% of tumor mass) were found in tumors grown in mice treated with THP (FIG. 13 B and FIG. 13D). On the other hand, control mice showed lower necrosis (30-35%, FIG. 13A and FIG. 13C) and disorganized in comparison to THP-treated tumors (FIG. 13B and FIG. 13D). A significant fibrotic area was observed in mice treated with THP (35%, FIG. 13B) meanwhile fibrosis was scarcely seen in control mice (10%, FIG. 13A). B16 tumors grown in control and THP-treated mice exhibit anaplasia (nuclear grade=3), high mitotic index (mitotic grade=3), poor differentiation (histological index=3) and show extensive intratumor vascularization (FIG. 13A-D). Renal morphology and structure showed a moderate cloudy degeneration of renal cortical tubular epithelium both in animals under THP treatment and control one. Pulmonary congestion and bronchiolar epithelium hyperplasia and splenomegalia with extramedullary hematopoiesis were observed in control and THP-treated mice.

The effect of s.c. administration of THP on the growth of the tumor cell line B16 is summarized in the following Table 3:

TABLE 3

Effect of s.c. administration of THP on B16 tumor growth

| Treatment THP (µg/kg/dose) | Mean tumor weight (g) ± SEM | Mean Growth Rate ± SEM (mm³/day) | % growth inhibition |
|---|---|---|---|
| Control | 791.2 ± 74.5 | 100.2 ± 11.3 | |
| 375 | 598.5 ± 51.4* | 82.1 ± 8.6 | 24 |
| 750 | 710.9 ± 49.5 | 104.6 ± 11.8 | 10 |
| 1500 | 691.3 ± 79.5 | 116.9 ± 16.5 | 12 |

*P < 0.05

When tumors reached 180.4±13.2 mm³, mice were treated as described in Materials and Methods. Each group contained 8 mice. Growth rate between day 1 of treatment and day 7, end of the experiment, was calculated as the slopes of growth curves. At the end of the experiment, tumor weight and percentage of growth inhibition in tumors from THP-treated mice with respect to vehicle-treated animals (control) was calculated as described in Materials and Methods.

Conclusion of the Report of Antitumor Effect of THP:

As it can be observed in the results shown in Table 1, THP inhibits 4T1 tumor growth in BALB/c mice receiving a dose of 187 µg/kg or higher. The highest values obtained in percentage of tumor growth inhibition are reached at doses of 187 µg/kg and 1500 µg/kg (highest value). Intermediate doses between 187 µg/kg and 1500 µg/kg showed a less percentage in tumor growth inhibition. It is important to clarify that mice appeared to tolerate treatment with THP without overt signs of toxicity and without variation of body weights in comparison with the control group.

As it can be observed in the results shown in Table 2, THP inhibits CT26 tumor growth in BALB/c mice receiving a dose higher than 750 µg/kg. The highest value obtained in percentage of tumor growth inhibition is reached at dose of 1500 µg/kg (highest value). It is important to clarify that mice appeared to tolerate treatment with THP without overt signs of toxicity and with a significant increasing of body weights in all groups including the control group.

As it can be observed in the results shown in Table 3, THP inhibits B16 tumor growth in C57BL mice receiving a dose of 375 µg/kg (highest value). The higher doses (750-1500 µg/kg) do not produce an increase in percentage of tumor growth inhibition. It is important to clarify that mice appeared to tolerate treatment with THP without overt signs of toxicity and with a significant increasing of body weights in all groups including the control group.

As conclusion of the above, THP could be used in treatment of different tumor cell lines in patients with tolerance without overt signs of toxicity.

FINAL CONCLUSION

Assay 1-6 demonstrate that the treatment with THP as a pegylated derivative inhibit the growing of ascitic sarcoma T 180, Solid SARCOMA-180, and produces an anti-infective action which increases the innate immune response in mammals. Similar results were obtained in the REPORT OF ANTITUMOR EFFECT OF THP respect to the inhibition of 4T1, CT26 and B16 tumor growth, confirming our previous observation in SARCOMA-180. The different tumor cell lines used inferred that THP can be effectively used in therapeutic administration to inhibit tumor growth.

It will be understood by those skilled in the art that the foregoing description and examples are illustrative of practicing the present invention, but are in no way limiting.

The invention claimed is:

1. A therapeutic method of treatment of breast adenocarcinoma in a mammal, wherein the breast adenocarcinoma has intratumor vascularization and the intratumor vascularization is retained after the therapeutic treatment, the method comprising parenterally administering to a mammal in need thereof a composition comprising an effective amount of human Tamm-Horsfall glycoprotein, native or pegylated, and a pharmacologically acceptable excipient.

2. The therapeutic method of treatment according to claim 1, wherein the human Tamm-Horsfall glycoprotein is a human Tamm-Horsfall glycoprotein pegylated with polyethylene glycol (PEG) tresylate.

3. A therapeutic method of treatment of breast cancer in a mammal, wherein the breast cancer has intratumor vascularization and the intratumor vascularization is retained after the therapeutic treatment, the method comprising parenterally administering to a mammal in need thereof a composition comprising an effective amount of human Tamm-Horsfall glycoprotein, native or pegylated, and a pharmacologically acceptable excipient.

* * * * *